US012779001B2

(12) United States Patent
Zhang et al.

(10) Patent No.: US 12,779,001 B2
(45) Date of Patent: Nov. 3, 2026

(54) APPLICATION OF TRADITIONAL CHINESE MEDICINE COMPOSITION IN PREPARATION OF DRUGS FOR TREATING NEURITIS

(71) Applicant: Shandong New Time Pharmaceutical Co., Ltd., Linyi (CN)

(72) Inventors: Guimin Zhang, Linyi (CN); Chenglei Sun, Linyi (CN); Jingchun Yao, Linyi (CN); Yongxia Guan, Linyi (CN); Qingwen Ma, Linyi (CN)

(73) Assignee: Shandong New Time Pharmaceutical Co., Ltd., Linyi (CN)

( * ) Notice: Subject to any disclaimer, the term of this patent is extended or adjusted under 35 U.S.C. 154(b) by 238 days.

(21) Appl. No.: 18/714,976

(22) PCT Filed: Dec. 1, 2022

(86) PCT No.: PCT/CN2022/135766
§ 371 (c)(1),
(2) Date: May 30, 2024

(87) PCT Pub. No.: WO2023/098776
PCT Pub. Date: Jun. 8, 2023

(65) Prior Publication Data

US 2025/0017994 A1 Jan. 16, 2025

(30) Foreign Application Priority Data

Dec. 3, 2021 (CN) ......................... 202111468002.X

(51) Int. Cl.

| | |
|---|---|
| ***A61K 36/076*** | (2006.01) |
| ***A61K 36/232*** | (2006.01) |
| ***A61K 36/233*** | (2006.01) |
| ***A61K 36/236*** | (2006.01) |
| ***A61K 36/237*** | (2006.01) |
| ***A61K 36/238*** | (2006.01) |
| ***A61K 36/346*** | (2006.01) |
| ***A61K 36/484*** | (2006.01) |
| ***A61K 36/538*** | (2006.01) |
| ***A61K 36/752*** | (2006.01) |
| ***A61P 25/02*** | (2006.01) |

(52) U.S. Cl.
CPC .......... *A61K 36/076* (2013.01); *A61K 36/232* (2013.01); *A61K 36/233* (2013.01); *A61K 36/236* (2013.01); *A61K 36/237* (2013.01); *A61K 36/238* (2013.01); *A61K 36/346* (2013.01); *A61K 36/484* (2013.01); *A61K 36/538* (2013.01); *A61K 36/752* (2013.01); *A61P 25/02* (2018.01)

(58) Field of Classification Search
None
See application file for complete search history.

(56) References Cited

FOREIGN PATENT DOCUMENTS

| | | | |
|---|---|---|---|
| CN | 1286105 | * | 3/2001 |
| CN | 1069004 | * | 8/2001 |
| CN | 1583066 | * | 2/2005 |
| CN | 103830685 | * | 6/2014 |
| CN | 108201592 A | | 6/2018 |
| CN | 112386635 | * | 2/2021 |
| CN | 112386635 A | | 2/2021 |
| CN | 114073730 A | | 2/2022 |

OTHER PUBLICATIONS

Egilmez et al. "Can covid-19 cause peripheral facial nerve palsy?". SN Comprehensive Clinical Medicine, published on May 22, 2021, (2021), 3, pp. 1707-1713.*
International Search Report mailed on Feb. 22, 2023 in PCT/CN2022/135766.
Chinese Written Opinion mailed on Feb. 22, 2023 in PCT/CN2022/135766.

* cited by examiner

*Primary Examiner* — Vera Afremova
(74) *Attorney, Agent, or Firm* — Fox Rothschild LLP

(57) ABSTRACT

A traditional Chinese medicine composition for treating neuritis. The traditional Chinese medicine composition is prepared mainly from *Notopterygii rhizoma* et *radix, Angelicae pubescentis radix, Poria, Saposhnikoviae radix, Schizonepetae herba, Chuanxiong rhizoma, Platycodonis radix, Bupleuri radix, Peucedani radix, Aurantii fructus*, and *Glycyrrhizae radix* et *rhizoma*. The traditional Chinese medicine composition can significantly relieve facial paralysis, movement disorders, and other related symptoms of facial neuritis in a rat, remarkably improve expression of VEGFb, VEGFR1, and VEGFR2 proteins in postoperative side facial nerves of the rat, and promote recovery and regeneration of damaged rear axons.

6 Claims, 3 Drawing Sheets

APPLICATION OF TRADITIONAL CHINESE MEDICINE COMPOSITION IN PREPARATION OF DRUGS FOR TREATING NEURITIS

CROSS-REFERENCE TO RELATED APPLICATIONS

The present disclosure is a National Stage filing under 35 U.S.C. 371 of International PCT Application No. PCT/CN2022/135766, filed on Dec. 1, 2022, which claims the priority of CN202111468002.X, filed on Dec. 3, 2021. The Chinese Patent Application No. CN202111468002.X is incorporated herein by reference as part of the disclosure of the present application.

TECHNICAL FIELD

The present invention pertains to the technical field of traditional Chinese medicine, and relates to a traditional Chinese medicine composition and its use, in particular to a traditional Chinese medicine composition and its use in preparing drugs for treating neuritis.

BACKGROUND

Neuritis refers to peripheral nerve disease, which is an organic disease of peripheral nervous system. According to the location and function of nerves, the nervous system can be divided into central nervous system and peripheral nervous system. Among them, facial neuritis is also called facial paralysis or facioplegia, which is facial muscle paralysis, mainly manifested as facial muscle movement obstruction. The clinical manifestations of facial paralysis are mainly bilateral facial paralysis with one severe side and one mild side and unilateral facial paralysis.

In traditional Chinese medicine, it is called facial distortion. It is due to the lack of healthy qi and poor collaterals of human body, and wind-evil takes advantage of weakness to enter Yangming vein of middle head and face, which leads to disharmony between nutrient qi and defensive qi on one side of face, obstruction of qi and blood, and loss of nourishment of meridians. It is divided into wind-cold syndrome and wind-heat syndrome.

The symptoms of wind-cold syndrome are sudden onset, skewed mouth, incomplete eyelid closure, fear of wind and aversion to cold, headache, stuffy nose, tight facial muscles, sore muscles and joints, reddish tongue, thin white fur and floating and tense pulse. The treatment method is to dispel wind and cold, eliminate phlegm and dredge collaterals. The main method is to apply Sanbai Wuchong Decoction: *Paeonia lactiflora pallas* 20 g, *Angelica dahurica* 15 g, *Rhizoma typhonii* 6 g, *Bombyx batryticatus* 15 g, *Cicada* slough 15 g, Fried earthworm 15 g, Scorpio 10 g, Centipede 2 (packed separately), *Saposhnikoviae radix* 10 g, *Chuanxiong rhizoma* 10 g, *Uncaria rhynchophylla* 20 g, *Astragalus membranaceus* 30 g. Decoct the above medicine in water twice except centipede, take it separately in the morning and evening, and take it once a day. Bake the centipede on tile, grind it into fine powder, and take it with water twice. In the prescription, *Saposhnikoviae radix, Angelica dahurica, Rhizoma typhonii* and *Uncaria rhynchophylla* can dispel wind and cold, and dredge collaterals, promote blood circulation and nourish nutrient qi, and "five insects" (i.e., centipede, scorpion, *Bombyx batryticatus, Cicada* slough and earthworm) can expel wind and dredge collaterals; *Paeonia lactiflora pallas* and *Chuanxiong rhizoma* can nourish blood, promote blood circulation and dispel wind; *Astragalus membranaceus* can tonify qi, strengthen body resistance and dispel wind, and all medicines are combined to eliminate pathogen and strengthen vital qi, eliminate wind and cold, nourish meridians, smooth blood vessels and heal facial paralysis.

The symptoms of wind-heat syndrome are sudden onset, skewed mouth and eyes, headache, hot face or fever, aversion to wind, upset, bitter taste, pain behind ears, dry mouth and sore throat, dry stool, yellow urine, red tongue tip, thin yellow fur and floating and tense pulse. The treatment method is to dispel wind and clear heat, promote blood circulation and dredge collaterals. The main method is to apply Jiawei Qianzheng Powder: Scorpion 7 g, *Rhizoma typhonii* 7 g, *Bombyx batryticatus* 7 g, Centipede 2, Earthworm 7 g, *Angelica sinensis* 10 g, *Paeonia lactiflora pallas* 10 g, *Chuanxiong Rhizoma* 10 g, *Saposhnikoviae radix* 10 g, *Uncaria rhynchophylla* 10 g, *Forsythia suspensa* 15 g, *Radix isatidis* 15 g and *Folium Isatidis* 15 g. In the prescription, with pungent flavor, warmness and summer-heat attributing to rise and dispersion, *Rhizoma typhonii* is a monarch drug for dispelling wind, eliminating phlegm and dredging collaterals and treating the wind of head and face; Scorpion, *Bombyx batryticatus* and earthworm can dispel wind and stop spasm, among which *Bombyx batryticatus* has the function of eliminating phlegm, and Scorpion is good at dredging collaterals; Centipede and *Uncaria rhynchophylla* can dispel wind and dredge collaterals; *Angelica sinensis, Paeonia lactiflora pallas, Chuanxiong rhizoma* and *Saposhnikoviae radix* can dispel wind and dredge collaterals, promote blood circulation and nourish nutrient qi, taking the meaning of "to cure wind, blood circulation shall be promoted first, and wind will be cured after good blood circulation", and *Forsythia suspensa, Radix isatidis* and *Folium isatidis* can clear heat, eliminate dampness and detoxify. The above medicines are combined to go through the meridians of the head and face, and reach the sick place directly to eliminate pathogen and strengthen vital qi.

CN108201592A discloses an oral traditional Chinese medicine preparation for treating facial paralysis caused by neuritis. The raw materials and parts by weight of the traditional Chinese medicine are *Bupleuri radix* 30 g, *Scutellaria baicalensis* 17 g, *Schizonepetae herba* 14 g, *Saposhnikoviae radix* 15 g, *Rhizoma typhonii* 15 g, *Gastrodia elata* 15 g, Scorpio 15 g, *Glycyrrhizae radix* et *rhizoma* 10 g, Garden balsam stem 15 g, *Notopterygii rhizoma* et *radix* 20 g and Earthworm 20 g. Although *Gastrodia elata* has a good effect of dredging meridians and activating collaterals, it has great toxic and side effects. In addition, Garden balsam stem has strong irritation, which is easy to stimulate intestines and stomach and damage gastric mucosa. The traditional Chinese medicine preparation provided by the present patent has a long treatment period, and the disease can be basically cured only after 11 courses of treatment.

At present, there are reports of treating facial neuritis with the modified prescription of *Schizonepetae herba* and *Saposhnikoviae radix* toxin-vanquishing powder.

The 5th edition of China News of Traditional Chinese Medicine published the modified prescription of *Schizonepetae herba* and *Saposhnikoviae radix* toxin-vanquishing powder to treat facial paralysis of meridian type stroke in wind-cold attack. First diagnosis: *Schizonepetae herba* 10 g, *Saposhnikoviae radix* 10 g, *Bupleuri radix* 12 g, *Scutellaria baicalensis* 10 g, *Notopterygii rhizoma* et *radix* 10 g, *Angelicae Pubescentis radix* 10 g, *Chuanxiong rhizoma* 12 g, Mint 10 g, Honeysuckle 10 g, *Forsythia suspensa* 10 g, *Angelica*

*dahurica* 10 g, *Pueraria lobata* 20 g, *Hedyotis diffusa* 15 g, Red paeony root 10 g, Great burdock achene 10 g and *Glycyrrhizae radix* et *rhizoma* 9 g. 2 doses. One dose a day in three times. Second diagnosis: *Angelicae pubescentis radix* and *Angelica dahurica* were removed from the original prescription, and *Angelica sinensis* 10 g, *Cicada* slough 6 g, *Rhizoma cimicifugae* 10 g, Great burdock achene 10 g and *Acorus gramineus* 10 g were added. 2 doses. Third diagnoses: Red paeony root 10 g, *Chuanxiong rhizoma* 6 g, *Angelica sinensis* 10 g, Earthworm 10 g, *Astragalus membranaceus* 20 g, *Pueraria lobata* 20 g, *Rhizoma cimicifugae* 10 g, *Cicada* slough 9 g, whole worm 6 g, *Radix clematidis* 20 g, *Hedyotis diffusa* 15 g, *Bombyx batryticatus* 10 g, Centipede 1 and *Glycyrrhizae radix* et *rhizoma* 6 g. 2 doses. One dose a day in three times. Fourth diagnoses: The above prescription is slightly adjusted, and 2 doses are used for prognosis. After 2 doses, there was no air leakage in the left corner of the mouth and no discomfort in the face. All the diseases were cured, and 8 doses were taken in total. In this report, the modified prescription of *Schizonepetae herba* and *Saposhnikoviae radix* toxin-vanquishing powder was selected and the disease was treated by stages according to syndrome differentiation. Although the treatment period was short, the prescription was changed every 2 doses, which increased the number of patients' inquiries and increased the probability of wind-cold attack.

JINGFANG Preparation is a modern ready-for-use traditional Chinese medicine preparation developed according to *Schizonepetae herba* and *Saposhnikoviae radix* toxin-vanquishing powder, which is prepared from *Notopterygii rhizoma* et *radix, Angelicae pubescentis radix, Poria, Saposhnikoviae radix, Schizonepetae herba, Chuanxiong rhizoma, Platycodonis radix, Bupleuri radix, Peucedani radix, Aurantii fructus* and *Glycyrrhizae radix* et *rhizoma. Saposhnikoviae radix, Schizonepetae herba* and *Notopterygii rhizoma* et *radix* is pungent-warm diaphoresis, which can dispel wind-cold, *Bupleuri radix* can strengthen relief of exterior syndrome, *Angelicae Pubescentis radix* can dispel wind and eliminate dampness, *Chuanxiong rhizoma* can promote blood circulation and dispel wind, and *Aurantii fructus* can regulate qi by alleviation of mental depression. The synergy of these drugs has the functions of dispelling wind and relieving exterior syndrome, promoting blood circulation and dredging collaterals, eliminating phlegm and killing toxin, clearing heat and eliminating dampness. At present, there is no report on the treatment of facial neuritis with JINGFANG Preparation.

SUMMARY

The present invention is a further development of the use of the existing products "JINGFANG KELI" and "JINGFANG HEJI". The new application comes from the feedback from employees of the company. Employees respond: After facial paralysis symptoms occur due to long-term air conditioning, they take JINGFANG KELI daily to prevent colds during routine treatment of facial neuritis, and find that facial paralysis symptoms are obviously relieved and the treatment period of facial neuritis is obviously shortened. Therefore, according to the feedback from employees, the applicant made further research on the use of JINGFANG Preparation in treating neuritis, especially facial neuritis.

The first purpose of the present invention is to provide a traditional Chinese medicine composition for treating neuritis, which comprises *Notopterygii rhizoma* et *radix, Angelicae pubescentis radix, Poria, Saposhnikoviae radix, Schizonepetae herba, Chuanxiong rhizoma, Platycodonis radix, Bupleuri radix, Peucedani radix, Aurantii fructus* and *Glycyrrhizae radix* et *rhizoma.*

Further, the traditional Chinese medicine composition comprises the following raw materials:

*Schizonepetae herba* 50-100 parts by weight, *Saposhnikoviae radix* 50-100 parts by weight, *Notopterygii rhizoma* et *radix* 50-100 parts by weight

*Angelicae Pubescentis radix* 50-100 parts by weight, *Bupleuri radix* 50-100 parts by weight, *Peucedani radix* 50-100 parts by weight

*Chuanxiong rhizoma* 50-100 parts by weight, *Aurantii fructus* 50-100 parts by weight, *Poria* 50-100 parts by weight

*Platycodonis radix* 50-100 parts by weight, and *Glycyrrhizae radix* et *rhizoma* 5-50 parts by weight.

Preferably, the traditional Chinese medicine composition comprises the following raw materials:

*Schizonepetae herba* 75 parts by weight, *Saposhnikoviae radix* 75 parts by weight, *Notopterygii rhizoma* et *radix* 75 parts by weight

*Angelicae Pubescentis radix* 75 parts by weight, *Bupleuri radix* 75 parts by weight, *Peucedani radix* 75 parts by weight

*Chuanxiong rhizoma* 75 parts by weight, *Aurantii fructus* 75 parts by weight, *Poria* 75 parts by weight

*Platycodonis radix* 75 parts by weight, and *Glycyrrhizae radix* et *rhizoma* 25 parts by weight.

The neuritis includes facial neuritis, trigeminal neuritis and polyneuritis.

The neuritis is caused by one or more of infection, poisoning, genetic defect, nutritional disorder, immune damage, metabolic disorder, endocrine disorder, congenital malformation, blood circulation disorder, abnormal hyperplasia, wind-cold and trauma.

Further, the traditional Chinese medicine composition can improve the symptoms of neuritis, and the symptoms include irritation symptoms and/or destruction symptoms, wherein the irritation symptoms show pain and numbness, and the destruction symptoms show weakness and paralysis.

Specifically, the neuritis is preferably facial neuritis, and the traditional Chinese medicine composition can improve the symptoms of facial neuritis, including shallow nasolabial groove, distortion of commissure, air leakage and salivation in speech, loss of facial random movements, large palpebral fissure, inability to successfully complete frowning, closing eyes, whistling and other movements, and loss of one or more facial expressions.

Further, the traditional Chinese medicine composition can be prepared with pharmaceutically acceptable excipients to form a preparation.

Specifically, the preparation comprises granules, mixtures, tablets, capsules, pills, dustpowders, powders, syrups, microcapsules and ointments, preferably JINGFANG KELI and JINGFANG HEJI.

The second purpose of the present invention is to provide the use of the JINGFANG Preparation in the preparation of a medicament for treating neuritis.

The third purpose of the present invention is to provide the use of the JINGFANG Preparation in the preparation of a medicament for treating facial neuritis.

The JINGFANG Preparation of the present invention includes but is not limited to JINGFANG KELI and JINGFANG HEJI, and the traditional Chinese medicine preparations prepared by adopting the traditional Chinese medicine composition of the present invention are all included in the JINGFANG Preparation category.

Compared with the prior art, the present invention has achieved remarkable technical effects:

(1) The traditional Chinese medicine composition of the present invention can obviously relieve facial paralysis, dyskinesia and other related symptoms of facial neuritis in rats.

(2) The traditional Chinese medicine composition of the present invention can significantly improve the expression of VEGFb, VEGFR1 and VEGFR2 proteins in lateral nerves of rats after operation, and promote the recovery and regeneration of axons after injury.

(3) The traditional Chinese medicine composition of the present invention can stimulate the electrical conduction of the facial nerve of rats and improve the electrical conduction speed of the facial nerve.

(4) The traditional Chinese medicine composition of the present invention can reduce the expression of Beclin1 protein in the facial nerve tissue of rats, increase the level of P62 protein, participate in the regulation mechanism of autophagy, and promote the functional recovery of facial nerve.

DETAILED DESCRIPTION OF THE PREFERRED EMBODIMENTS

Figure 1:
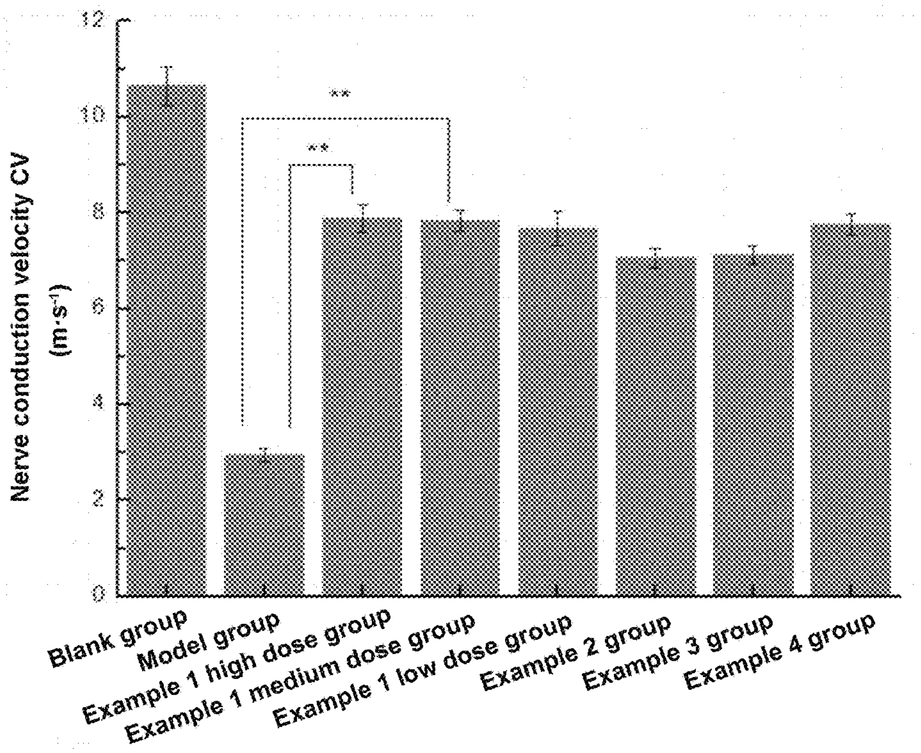
FIG. 1-2: Study on Nerve Conduction Velocity of Lateral Nerve Potential of Rats in Each Group after Administration for 14 Days

The summary of the present invention is described in further detail by way of examples in order to make the purse and the technical proposal of the present invention clearer, but it should not be understood that the scope of the above subject area of the present invention is limited to the following examples. Corresponding substitutions or modifications made in accordance with ordinary knowledge and conventional means in the art without departing from the above-mentioned techniques of the present invention are included in the present invention.

Example 1 Preparation of Granule (Commercially Available JINGFANG KELI)

Prescription:

*Schizonepetae herba* 75 g, *Saposhnikoviae radix* 75 g, *Notopterygii rhizoma* et *Radix* 75 g, *Angelicae Pubescentis radix* 75 g, *Peucedani radix* 75 g

*Chuanxiong rhizoma* 75 g, *Aurantii fructus* 75 g, *Poria* 75 g, *Platycodonis radix* 75 g, and *Glycyrrhizae radix* et *rhizoma* 25 g;

Preparation Method:

Among the above eleven herbs, extract volatile oils of *Schizonepetae herba, Saposhnikoviae radix, Notopterygii rhizoma* et *radix, Angelicae pubescentis radix, Peucedani radix, Chuanxiong rhizoma* and *Aurantii fructus* respectively, and collect the distilled aqueous solution of *Chuanxiong rhizoma* and *Aurantii fructus* separately; percolate the residues of *Chuanxiong rhizoma, Aurantii fructus* and *Poria* with 25% ethanol solution prepared from the above aqueous solution as solvent according to the percolation method under the terms of fluid extract and extract; decoct the residues of *Schizonepetae herba, Saposhnikoviae radix, Notopterygii rhizoma* et *radix, Angelicae Pubescentis radix* and *Peucedani radix* together with the rest of *Bupleuri radix, Platycodonis radix* and *Glycyrrhizae radix* et *rhizoma* in water for 1.5 hours twice, combine decoction, filter, and concentrate filtrate into thick paste; combine the percolated liquid and the thick paste, mix evenly, stand, filter, concentrate the filtrate into clear paste with a relative density of 1.30 (80-85° C.), take 1 part of the clear paste, add 6 parts of sucrose, mix evenly to make granules, dry, add the volatile oils such as *Schizonepetae herba*, and mix evenly.

Example 2 Preparation of Granule

Prescription:

*Schizonepetae herba* 50 g, *Saposhnikoviae radix* 50 g, *Notopterygii rhizoma* et *Radix* 50 g, *Angelicae Pubescentis radix* 50 g, *Peucedani radix* 50 g

*Chuanxiong rhizoma* 50 g, *Aurantii fructus* 50 g, *Poria* 50 g, *Platycodonis radix* 50 g, and *Glycyrrhizae radix* et *rhizoma* 5 g.

Preparation Method: Same as Example 1.

Example 3 Preparation of Granule

Prescription:

*Schizonepetae herba* 100 g, *Saposhnikoviae radix* 100 g, *Notopterygii rhizoma* et *Radix* 100 g, *Angelicae Pubescentis radix* 100 g, *Peucedani radix* 100 g

*Chuanxiong rhizoma* 100 g, *Aurantii fructus* 100 g, *Poria* 100 g, *Platycodonis radix* 100 g, and *Glycyrrhizae radix* et *rhizoma* 50 g.

Preparation Method: Same as Example 1.

Example 4 Preparation of Mixture (Commercially Available JINGFANG HEJI)

Prescription:

*Schizonepetae herba* 97 g, *Saposhnikoviae radix* 97 g, *Notopterygii rhizoma* et *Radix* 97 g, *Angelicae Pubescentis radix* 97 g, *Peucedani radix* 97 g

*Chuanxiong rhizoma* 97 g, *Aurantii fructus* 97 g, *Poria* 97 g, *Platycodonis radix* 97 g, and *Glycyrrhizae radix* et *rhizoma* 32.4 g;

Preparation Method:

Distill *Schizonepetae herba, Saposhnikoviae radix, Notopterygii rhizoma* et *radix, Angelicae pubescentis radix, Aurantii fructus, Chuanxiong rhizoma* and *Peucedani Radix* and extract volatile oils respectively, and collect the distilled aqueous solution separately; percolate the residues of *Chuanxiong rhizoma, Aurantii fructus* and *Poria* with 25% ethanol solution prepared from the above aqueous solution as solvent according to the percolation method under the terms of fluid extract and extract, collect percolate and recover ethanol under reduced pressure. Decoct the remaining five kinds of residues with *Bupleuri radix, Platycodonis radix* and *Glycyrrhizae radix* et *rhizoma* in water for three times, filter, combine filtrate, concentrate to about 1300 mL, combine with percolate, stand still, filter, concentrate to about 1000 mL, add 3 g of sodium benzoate and the above volatile oil, stir evenly, and add water to make it 1000 mL.

Comparative Example 1: Decoction

*Bupleuri radix* 30 g, *Scutellaria baicalensis* 17 g, *Schizonepetae herba* 14 g, *Saposhnikoviae radix* 15 g, *Rhizoma typhonii* 15 g, *Gastrodia elata* 15 g Scorpion 15 g, *Glycyrrhizae radix* et *rhizoma* 10 g, Garden balsam stem 15 g, *Notopterygii rhizoma* et *radix* 20 g, Earthworm 20 g Preparation Method:

Prepare decoction to 500 mL by conventional decoction.

Comparative Example 2: Decoction

*Schizonepetae herba* 10 g, *Saposhnikoviae radix* 10 g, *Bupleuri radix* 12 g, *Scutellaria baicalensis* 10 g, *Notopterygii rhizoma* et *radix* 10 g, *Angelicae Pubescentis Radix* 10 g, *Chuanxiong rhizoma* 12 g Mint 10 g, Honeysuckle 10 g, *Forsythia suspensa* 10 g, *Angelica dahurica* 10 g, *Pueraria lobata* 20 g, *Hedyotis diffusa* 15 g Red paeony root 10 g, Great burdock achene 10 g and *Glycyrrhizae radix* et *rhizoma* 9 g Preparation method: Prepare decoction to 500 mL by conventional decoction.

Comparative Example 3: Decoction

*Schizonepetae herba* 10 g, *Saposhnikoviae radix* 10 g, *Bupleuri radix* 12 g, *Scutellaria baicalensis* 10 g, *Notopterygii rhizoma* et *radix* 10 g, *Chuanxiong rhizoma* 12 g, *Angelica sinensis* 10 g Mint 10 g, Honeysuckle 10 g, *Forsythia suspensa* 10 g, *Pueraria lobata* 20 g, *Hedyotis diffusa* 15 g, *Cicada* slough 6 g Red paeony root 10 g, Great burdock achene 10 g, *Glycyrrhizae radix* et *rhizoma* 9 g, *Rhizoma cimicifugae* 10 g, Great burdock achene 10 g, and *Acorus gramineus* 10 g Preparation method: Prepare decoction to 500 mL by conventional decoction.

Pharmacological Experiment

The inventor carried out related pharmacodynamic experimental research to prove the efficacy of JINGFANG Preparation in the present invention in treating facial neuritis. It should be noted that the following experimental studies are carried out on the basis of proving drug safety by acute toxicity test and long-term toxicity test, and the dosage in the experimental studies is within the safe dose range. The medicines selected in the following pharmacodynamic tests are prepared from the representative formula of the present invention; pharmacodynamic experiments have also been carried out by the inventor of the medicines prepared from other formulations contained in the present invention, and the experimental results have the same or similar effects, but due to space limitations, they are not listed here.

In addition, the following pharmacodynamic experiments only take some animal models as examples to verify the efficacy of the present invention. Here, only the pharmacodynamic experimental results of the traditional Chinese medicine composition for treating facial neuritis are displayed. The inventor has also done relevant pharmacodynamic experiments for neuritis caused by other types and other pathogenic factors mentioned in the present invention, and the experimental results show the same or similar effects, so the pharmacodynamic experimental results will not be listed one by one.

1 Materials 1.1 Experimental Drugs and Reagents 1.1.1 Drugs

Granules obtained in Examples 1, 2 and 3 of the present invention;

Example 4 Mixture;

Decoctions obtained in Comparative examples 1-3.

1.1.2 Dose

Example 1 Granule: 2.02 g/kg (low dose), 4.05 g/kg (medium dose), 8.10 g/kg (high dose);

Example 2 Granule: 4.05 g/kg;

Example 3 Granule: 4.05 g/kg;

Example 4 Mixture: 4.05 ml/kg;

Decoction in Comparative example 1: 18 mL/kg;

Decoction in Comparative example 2: 18 mL/kg;

Decoction in Comparative example 3: 18 mL/kg;

1.2 Experimental Animals

SD rats, SPF grade, 180-220 g, experimental animal license number: SYXK (Lu) 20180008, provided by Lunan Pharmaceutical Group Co., Ltd., were fed adaptively under standard conditions for one week before the experiment.

2. Methods 2.1 Molding Method and Grouping

A number of rats, half male and half female, were taken. An appropriate amount of ether was poured into the small beaker to completely infiltrate the cotton ball, and the small beaker was put into the rat anesthesia chamber after the ether container was tightly covered. Then, the rat is quickly put into the anesthesia chamber before the anesthesia chamber is closed tightly. When the rats fell spontaneously and fast breathing slowed down, they were taken out of the anesthesia chamber to check their corneal reflexes and pain reflexes. If the rat did not close their eyes and dodge when touching their cornea with the tip of the hemostat, it was proved that the corneal reflexes disappeared; if the rat did not struggle or dodge when clamping the toe of the rat with appropriate force with a hemostat, it was proved that the pain reflexes disappeared and the rats' general anesthesia was effective. Then, the right side of the rat was fixed upwards on the surgical table in a lateral position because the right side of the face is the surgical area to be sterilized with 1% iodophor solution. A cortex of about 1 cm long was cut at the midpoint of the line connecting the right tragus and the pupil of the right eye of the rat, with the incision perpendicular to the connecting line. After the subcutaneous tissue of the incision was separated to the muscular surface, the facial nerve was separated along the exposed buccal branch of the rat facial nerve towards the right auricle of the rat until the right facial nerve stem of the rat was exposed. The facial nerve was separated and clamped with the front end of the needle holder for 90 s. After the clamping damage was formed, the wound was sutured with 3-0 silk suture, and applied with erythromycin ointment to prevent infection. The modeled rats were taken to form the model group, three dose groups of Example 1 (high, medium, and low), the groups of Examples 2-4, and the groups of Comparative examples 1-3, with 10 rats in each group, half male and half female. The operation of 10 rats in the blank group (half male and half female) was basically the same as above, but the right facial nerve stem was only exposed without any injury treatment.

2.2 Administration

Rats in each administration group are given corresponding drugs by intragastric administration, while rats in the blank group and model group are given the same amount of normal saline by intragastric administration once a day for 14 days.

3. Statistical Processing

SPSS 22.0 software is used for statistical analysis of the data. The measurement data are expressed by (x+s). One-way ANOVA is used for comparison among multiple groups, and independent sample T test is used for analysis between two groups. The difference is statistically significant with $P<0.05$.

4 Observation Indexes and Experimental Results 4.1 Rat Behavioral Score 4.1.1 Scoring Criteria

TABLE 1

| Scoring Table of Tentacle Movement | | |
|---|---|---|
| Score | Tentacle movement | Position of tentacle |
| 1 | No tentacle movement | Backward |
| 2 | Mild tremor | Backward |
| 3 | Large tremor | Backward |
| 4 | Normal tentacle movement | Backward |
| 5 | Normal | Forward |

TABLE 2

| Observation Table of Eye Closure and Blink Reflex | |
|---|---|
| Score | Blink reflex and eye closure |
| 1 | No blink reflex or eye closure |
| 2 | Ocular muscle tension with no blink reflex |
| 3 | Blink reflex with 50% eye closure |
| 4 | Blink reflex with 75% eye closure |
| 5 | Complete closure, positive blink reflex |

4.1.2 Statistical Results

TABLE 3

Behavioral Scores of Rats after Administration on 0 d ($\bar{x}$ ± s, n = 10)

| Group | | Behavioral score 0 d |
|---|---|---|
| Blank group | | 9.79 ± 0.51 |
| Model group | | 1.71 ± 0.54* |
| Example 1 | High dose group | 1.68 ± 0.44* |
| | Medium dose group | 1.73 ± 0.49* |
| | Low dose group | 1.72 ± 0.36* |
| Example 2 group | | 1.75 ± 0.46* |
| Example 3 group | | 1.69 ± 0.48* |
| Example 4 group | | 1.68 ± 0.58* |
| Comparative example 1 group | | 1.71 ± 0.52* |
| Comparative example 2 group | | 1.73 ± 0.50* |
| Comparative example 3 group | | 1.70 ± 0.41* |

Note:
Compared with the blank group,
*P < 0.01.

TABLE 4

Behavioral Scores of Rats after Administration for 14 d ($\bar{x}$ ± s, n = 10)

| Group | | Behavioral score 14 d |
|---|---|---|
| Blank group | | 9.80 ± 0.42 |
| Model group | | 2.20 ± 0.82* |
| Example 1 | High dose group | 6.68 ± 0.97*# |
| | Medium dose group | 6.65 ± 0.88*# |
| | Low dose group | 5.10 ± 1.06*# |
| Example 2 group | | 5.40 ± 1.03*# |
| Example 3 group | | 5.90 ± 0.97*# |
| Example 4 group | | 6.80 ± 1.05*# |
| Comparative example 1 group | | 3.30 ± 1.42*# |
| Comparative example 2 group | | 4.20 ± 1.40*# |
| Comparative example 3 group | | 3.70 ± 1.34*# |

Note:
Compared with the blank group,
*P < 0.01;
Compared with the model group,
#P < 0.01.

The results of behavioral scores of facial neuritis showed that among the comparison between the blank group and model group, three dose groups (high, medium, low) in Example 1, Example 2-4 groups, and Comparative example 1-4 groups after administration on Od, the difference was statistically significant (P<0.01), which proved that the model was successful; on the 14th day of administration, among the model group and blank group, three dose groups (high, medium and low) in Example 1, Example 2-4 groups, and Comparative example 1-4 groups respectively, the difference was statistically significant (P<0.01).

4.2 Expression of VEGFb, VEGFR1 and VEGFR2 Protein in Lateral Nerves of Rats after Administration for 14 Days

TABLE 5

Expression of VEGFb Protein in Lateral Nerves of Rats after Administration for 14 Days ($\bar{x}$ ± s, n = 10)

| Group | | VEGFb/Actin |
|---|---|---|
| Blank group | | 1.72 ± 0.07 |
| Model group | | 0.76 ± 0.06 |
| Example 1 | High dose group | 1.59 ± 0.15*# |
| | Medium dose group | 1.58 ± 0.14*# |
| | Low dose group | 1.19 ± 0.13*# |
| Example 2 group | | 1.25 ± 0.09*# |
| Example 3 group | | 1.46 ± 0.11*# |
| Example 4 group | | 1.62 ± 0.11*# |
| Comparative example 1 group | | 0.92 ± 0.12*% |
| Comparative example 2 group | | 1.06 ± 0.14*# |
| Comparative example 3 group | | 0.98 ± 0.11*# |

Note:
Compared with the blank group,
*P < 0.01;
Compared with the model group,
#P < 0.01,
%P < 0.05.

TABLE 6

Expression of VEGFR1 Protein in Lateral Nerves of Rats after Administration for 14 Days ($\bar{x}$ ± s, n = 10)

| Group | | VEGFR1/Actin |
|---|---|---|
| Blank group | | 1.58 ± 0.05 |
| Model group | | 0.68 ± 0.04 |
| Example 1 | High dose group | 1.36 ± 0.14*# |
| | Medium dose group | 1.35 ± 0.10*# |
| | Low dose group | 1.05 ± 0.05*# |
| Example 2 group | | 1.13 ± 0.15*# |
| Example 3 group | | 1.27 ± 0.15*# |
| Example 4 group | | 1.38 ± 0.09*# |
| Comparative example 1 group | | 0.86 ± 0.15*# |
| Comparative example 2 group | | 0.95 ± 0.12*# |
| Comparative example 3 group | | 0.89 ± 0.13*# |

Note:
Compared with the blank group,
*P < 0.01;
Compared with the model group,
#P < 0.01.

TABLE 7

Expression of VEGFR2 Protein in Lateral Nerves of Rats after Administration for 14 Days ($\bar{x}$ ± s, n = 10)

| Group | | VEGFR2/Actin |
|---|---|---|
| Blank group | | 1.56 ± 0.03 |
| Model group | | 0.61 ± 0.05 |
| Example 1 | High dose group | 1.53 ± 0.15*# |
| | Medium dose group | 1.54 ± 0.13*# |

TABLE 7-continued

Expression of VEGFR2 Protein in Lateral Nerves of Rats after Administration for 14 Days ($\bar{x} \pm s$, n = 10)

| Group | VEGFR2/Actin |
|---|---|
| Low dose group | 1.27 ± 0.12*# |
| Example 2 group | 1.36 ± 0.14*# |
| Example 3 group | 1.43 ± 0.13*# |
| Example 4 group | 1.55 ± 0.08*# |
| Comparative example 1 group | 0.99 ± 0.08*# |
| Comparative example 2 group | 1.09 ± 0.05*# |
| Comparative example 3 group | 1.04 ± 0.08*# |

Note:
Compared with the blank group,
*P < 0.01;
Compared with the model group,
#P < 0.01.

To sum up, according to the pharmacodynamic experimental results, the traditional Chinese medicine composition of the present invention can obviously relieve the facial paralysis related symptoms of facial neuritis, significantly improve the expression of VEGFb, VEGFR1 and VEGFR2 proteins in the lateral nerves of rats after operation, promote the recovery and regeneration of axons after injury, and effectively treat facial neuritis.

4.3 Study on Nerve Conduction Velocity of Lateral Nerve Potential of Rats after Administration for 14 Days After administration for 14 days, rats were anesthetized by intraperitoneal injection, and facial nerves were separated. Stimulating electrodes and recording electrodes were placed along the separated facial nerves from proximal to distal. Nerve conduction velocity CV ($m \cdot s^{-1}$)=distance between stimulating electrodes and recording electrodes/conduction time. The mean value was calculated by repeated measurement for 10 times.

As shown in FIG. 1, after administration for 14 days, the rats in each group were compared in potential nerve conduction velocity test, which showed that among the comparison between the model group and blank group, three dose groups (high, medium and low) in Example 1, and Example 2-4 groups respectively, the difference was statistically significant (P<0.01).

Figure 2:
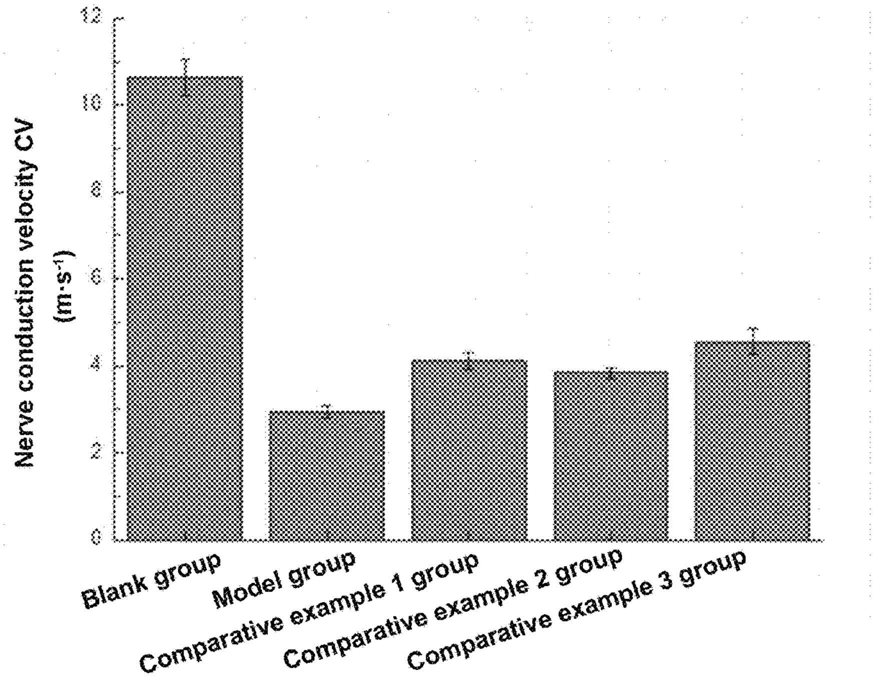
Figure 3:
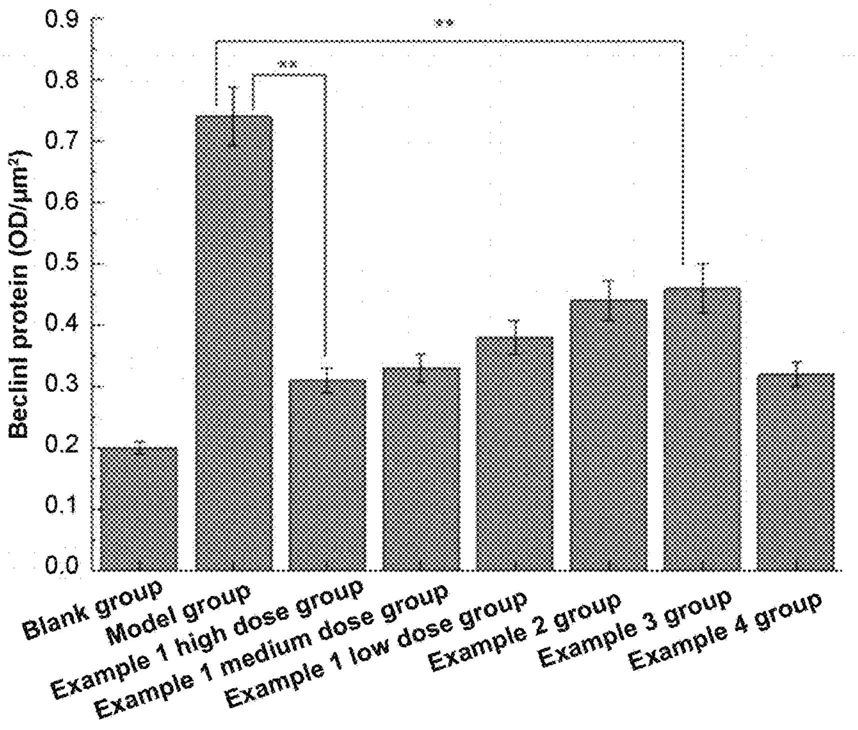
FIG. 3-4: Expression of Beclin1 Protein in Facial Nerve Tissue of Rats in Each Group after Administration for 14 Days
Figure 4:
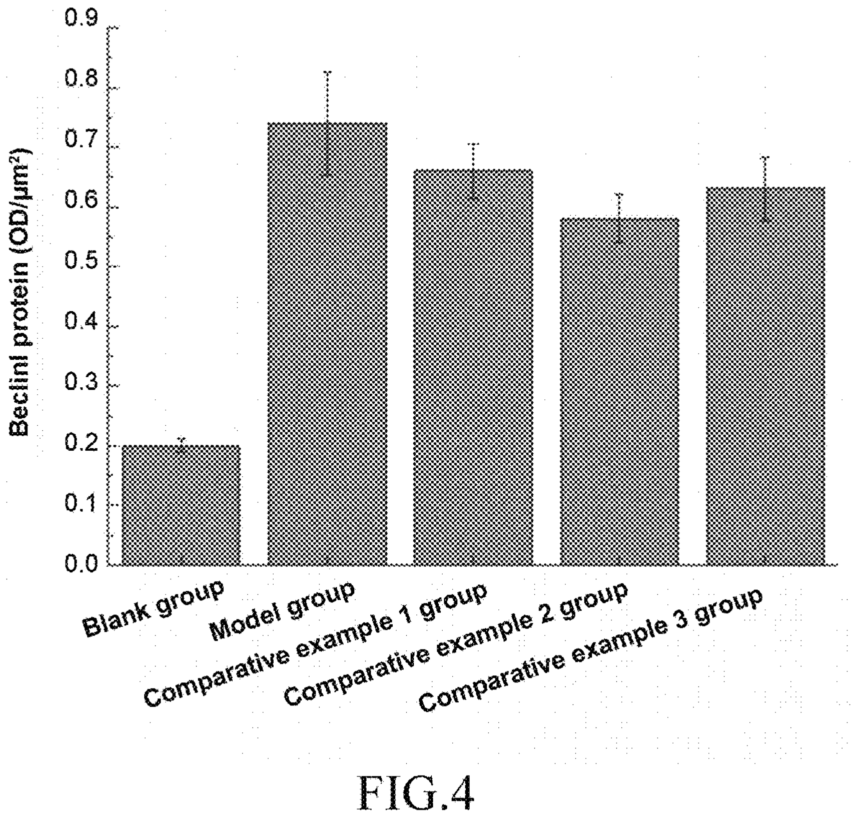
Figure 5:
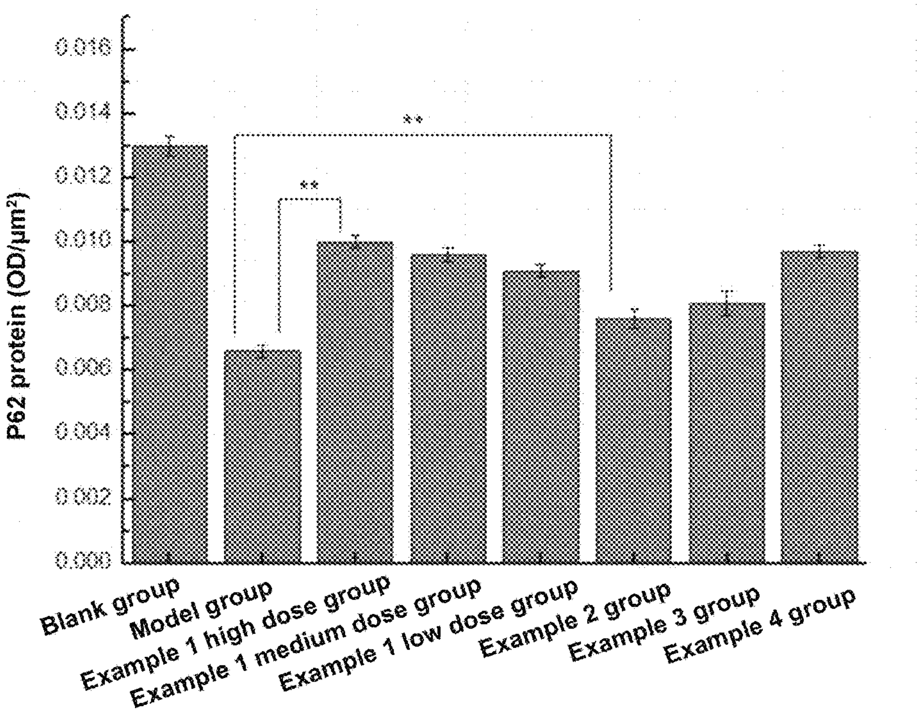
FIG. 5-6: Expression of P62 Protein in Facial Nerve Tissue of Rats in Each Group after Administration for 14 Days
Figure 6:
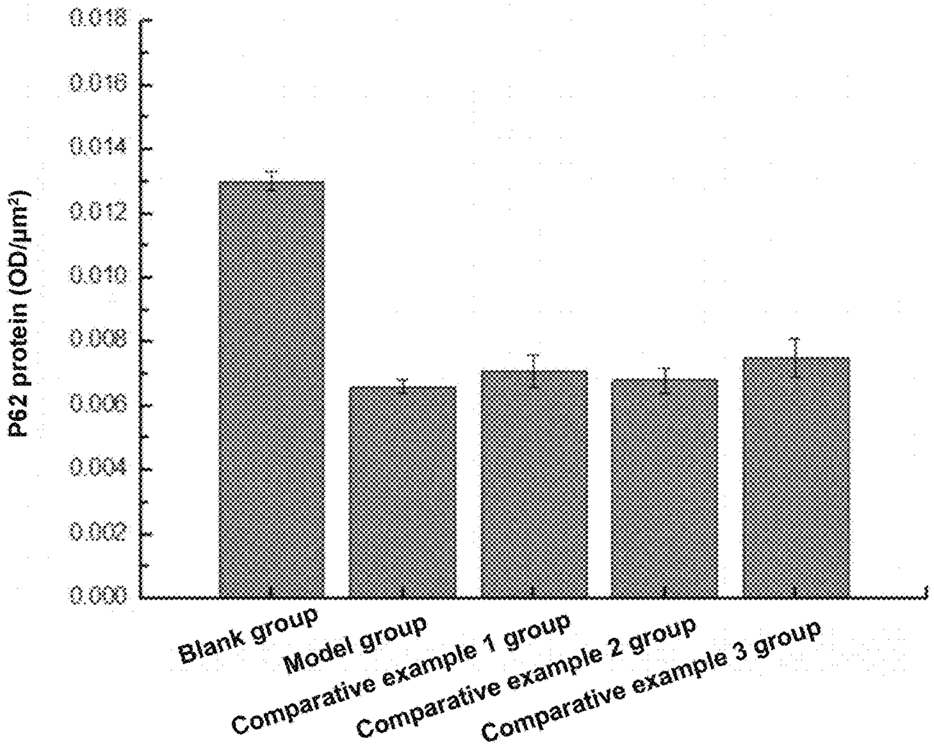

FIG. 2 is a comparison of facial nerve conduction velocity of rats in Comparative examples 1-3, model group and blank group. Comprehensive comparison shows that the traditional Chinese medicine composition of the examples of the present invention can stimulate electrical conduction of facial nerve of rats and effectively treat facial neuritis.

4.4 Expression of Beclin1 Protein and P62 Protein in Facial Nerve Tissue of Rats After administration for 14 days, the expression of Beclin1 protein in facial nerve tissue was detected by immunohistochemistry and P62 protein in facial nerve tissue was detected by RT-PCR.

FIG. 3, FIG. 4, FIG. 5 and FIG. 6 show the expression levels of Beclin1 protein and P62 protein in facial nerve tissue of rats after administration for 14 days. The results showed that the traditional Chinese medicine composition of the present invention can reduce the expression of Beclin1 protein in the facial nerve tissue of rats, increase the level of P62 protein, participate in the regulation mechanism of autophagy, and promote the recovery of facial nerve function. Among the comparison between the model group and blank group, three dose groups (high, medium and low) in Example 1, and Example 2-4 groups respectively, the difference was statistically significant (P<0.01).

To sum up, through the behavior score of rats, it can be seen that the traditional Chinese medicine composition of the present invention can obviously relieve facial paralysis, dyskinesia and other related symptoms of facial neuritis of rats; can significantly increase the expression of VEGFb, VEGFR1 and VEGFR2 proteins in the lateral nerve of rats after operation, promote the recovery and regeneration of axons after injury, stimulate the electrical conduction of facial nerve in rats, improve the electrical conduction velocity of facial nerve, reduce the expression of Beclin1 protein in facial nerve tissue of rats, increase the level of P62 protein, and promote the recovery of facial nerve function. Therefore, the traditional Chinese medicine composition of the present invention has the effect of treating facial neuritis and can improve the related symptoms of facial neuritis.

The invention claimed is:

1. A method for treating facial neuritis in a subject, comprising administering a therapeutically effective amount of a traditional Chinese medicine composition to the subject, wherein the traditional Chinese medicinal composition consists of the following traditional Chinese medicine components: *Notopterygii rhizoma* et *radix* 50-100 parts by weight, *Angelicae Pubescentis radix* 50-100 parts by weight, *Poria* 50-100 parts by weight, *Saposhnikoviae radix* 50-100 parts by weight, *Schizonepetae herba* 50-100 parts by weight, *Chuanxiong rhizoma* 50-100 parts by weight, *Platycodonis radix* 50-100 parts by weight, *Bupleuri radix* 50-100 parts by weight, *Peucedani radix* 50-100 parts by weight, *Aurantii fructus* 50-100 parts by weight and *Glycyrrhizae radix* et *rhizoma* 5-50 parts by weight.

2. The method according to claim 1, characterized in that the traditional Chinese medicine composition consists of the following traditional Chinese medicine components:

*Schizonepetae herba* 75 parts by weight, *Saposhnikoviae radix* 75 parts by weight, *Notopterygii rhizoma* et *radix* 75 parts by weight,

*Angelicae Pubescentis radix* 75 parts by weight, *Bupleuri radix* 75 parts by weight, *Peucedani radix* 75 parts by weight,

*Chuanxiong rhizoma* 75 parts by weight, *Aurantii fructus* 75 parts by weight, *Poria* 75 parts by weight,

*Platycodonis radix* 75 parts by weight, and *Glycyrrhizae radix* et *rhizoma* 25 parts by weight.

3. The method according to claim 1, characterized in that the neuritis is caused by one or more of poisoning, genetic defect, nutritional disorder, immune damage, metabolic disorder, endocrine disorder, congenital malformation, blood circulation disorder, abnormal hyperplasia, wind-cold and trauma.

4. The method according to claim 1, characterized in that the traditional Chinese medicine composition can improve the symptoms of neuritis, and the symptoms include irritation symptoms and/or destruction symptoms, wherein the irritation symptoms show pain and numbness, and the destruction symptoms show weakness and paralysis.

5. The method according to claim 1, characterized in that the traditional Chinese medicine composition can improve the symptoms of facial neuritis, including shallow nasolabial groove, distortion of commissure, air leakage and salivation in speech, loss of facial random movements, large palpebral fissure, inability to successfully complete frowning, closing eyes, whistling and other movements, and loss of one or more facial expressions.

6. The method according to claim 1, characterized in that the traditional Chinese medicine composition can be prepared into a preparation with pharmaceutically acceptable excipients; and the preparation comprises granules, mixtures, tablets, capsules, pills, dust powders, powders, syrups, microcapsules and ointments.

* * * * *